US009453843B2

(12) United States Patent  (10) Patent No.: US 9,453,843 B2
Fontaine et al.  (45) Date of Patent: Sep. 27, 2016

(54) MULTIFUNCTIONAL COUPLING REAGENTS HAVING AN AZLACTONE FUNCTION

(71) Applicants: CENTRE NATIONAL DE LA RECHERCHE SCIENTIFIQUE, Paris (FR); UNIVERSITE DU MAINE, Le Mans (FR)

(72) Inventors: Laurent Fontaine, Le Mans (FR); The Hien Ho, Herouville Saint Clair (FR); Sagrario Pascual, Le Mans (FR); Veronique Montembault, Le Mans (FR)

(73) Assignees: CENTRE NATIONAL DE LA RECHERCHE SCIENTIFIQUE, Paris (FR); UNIVERSITE DU MANS, Le Mans (FR)

( * ) Notice: Subject to any disclaimer, the term of this patent is extended or adjusted under 35 U.S.C. 154(b) by 0 days.

(21) Appl. No.: 14/436,942

(22) PCT Filed: Oct. 14, 2013

(86) PCT No.: PCT/EP2013/071430
§ 371 (c)(1),
(2) Date: Apr. 20, 2015

(87) PCT Pub. No.: WO2014/060357
PCT Pub. Date: Apr. 24, 2014

(65) Prior Publication Data
US 2015/0285811 A1 Oct. 8, 2015

(30) Foreign Application Priority Data
Oct. 18, 2012 (FR) ...................... 12 59941

(51) Int. Cl.
*C07D 263/42* (2006.01)
*G01N 33/58* (2006.01)
*A61K 47/48* (2006.01)
(52) U.S. Cl.
CPC ......... *G01N 33/58* (2013.01); *A61K 47/48061* (2013.01); *C07D 263/42* (2013.01); *Y10T 436/143333* (2015.01)

(58) Field of Classification Search
None
See application file for complete search history.

(56) References Cited

U.S. PATENT DOCUMENTS

| 5,344,701 | A | 9/1994 | Gagnon et al. |
| 5,451,453 | A | 9/1995 | Gagnon et al. |
| 6,762,257 | B1 | 7/2004 | Lewandowski et al. |
| 6,894,133 | B2 | 5/2005 | Lewandowski et al. |
| 6,906,158 | B2 * | 6/2005 | Tully ...................... C08F 26/06 526/258 |
| 2004/0242840 | A1 | 12/2004 | Tully |

FOREIGN PATENT DOCUMENTS

| WO | 9325594 | 12/1993 |
| WO | 2004081538 | 9/2004 |

OTHER PUBLICATIONS

French search report, dated May 21, 2013, in corresponding French Patent Application No. 1259941.
Sola, Jordi, et al., "Nanometer-Range Communication of Stereochemical Information by Reversible Switching of Molecular Helicity," Angewandte Chemie International Edition, 2010 (49), pp. 6386-6389.
Kolb, Hartmuth C., et al., "Click Chemistry: Diverse Chemical Function from a Few Good Reactions," Angewandte Chemie International Edition, 2001 (40), pp. 2004-2021.
International search report, dated Feb. 26, 2014, in Application No. PCT/EP2013/071430.

* cited by examiner

*Primary Examiner* — Kamal Saeed
(74) *Attorney, Agent, or Firm* — Young & Thompson

(57) ABSTRACT

Novel compounds, having an azlactone function, of formula (I), to be used as multifunctional coupling agents, and a method for coupling a biomolecule and a target molecule using such a compound are described. A diagnosis reagent, a kit for implementing the coupling method, a method for separating, detecting and/or characterizing at least one molecule of interest, and a composition including a novel compound are also described.

11 Claims, 1 Drawing Sheet

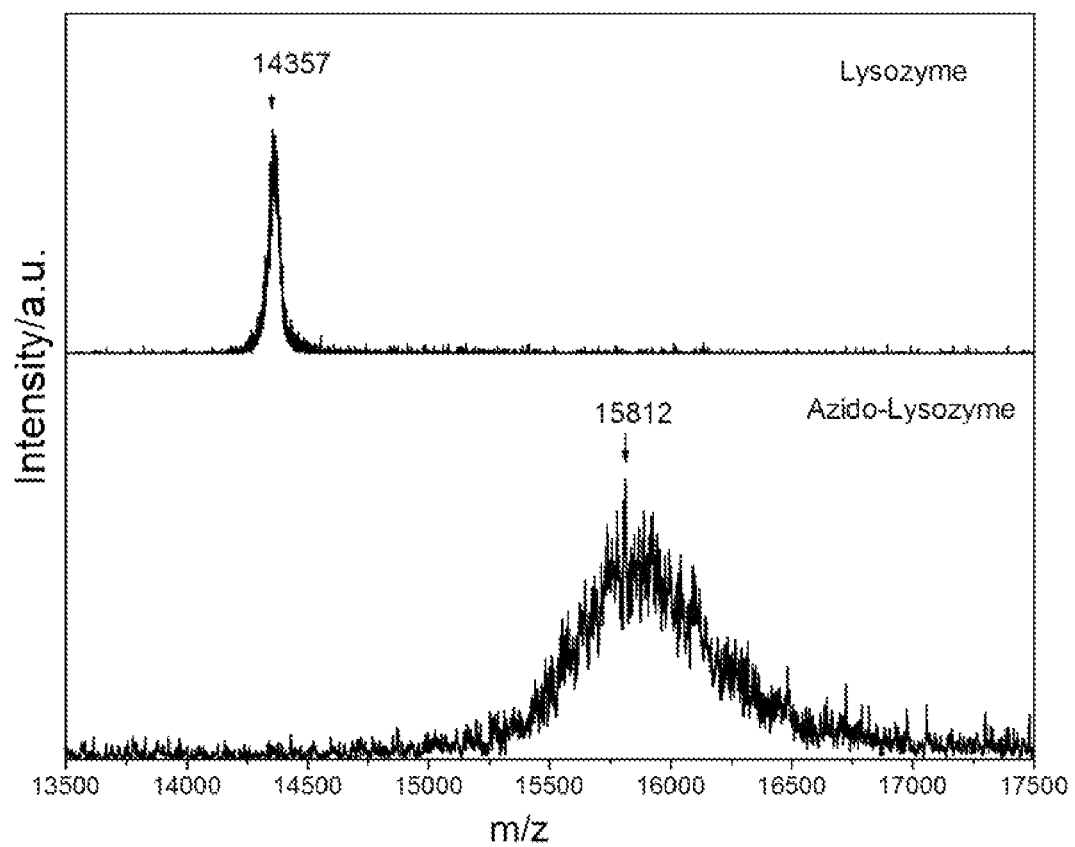

MULTIFUNCTIONAL COUPLING REAGENTS HAVING AN AZLACTONE FUNCTION

A subject of the present invention is novel multifunctional compounds, and their use in click chemistry in a method for coupling a biomolecule and a target molecule.

The field of the invention is the design and the synthesis of molecules having at least two distinct reactive chemical functions making it possible to carry out chemistry reactions called "click" reactions between biomolecules containing primary amine groups such as proteins, nucleic acids or certain polysaccharides.

Currently a very high demand exists in the field of bioconjugation or ligation of biomolecules with natural or synthetic polymers, because of the potential applications of such bioconjugates in biology, biochemistry, biotechnologies and nanomedicine.

The immense complexity and diversity of life represents an enormous challenge for the scientists trying to discover its chemical base. The decoding of the genetic composition of different organisms is not entirely useful if it is not accompanied by knowledge of the function of the encoded proteins. Bioconjugation which consists of coupling two biomolecules by a covalent bond is a means of achieving this goal.

In particular, bioconjugation represents a useful approach for understanding the regulation and the biological function of certain proteins and certain biopolymers by the binding of ligands. This approach consists of attaching small synthetic or natural molecules, which can function like probes, to the molecules of biological interest in order to monitor the binding of the ligand. Such probes include for example fluorescent molecules, biotin and Nuclear Magnetic Resonance (NMR) probes. This technique offers the possibility of rapidly testing a large number of potential ligands. Another approach consists of introducing synthetic functional groups onto biomolecules, a step which is followed by their immobilization on surfaces by a chemoselective reaction. The immobilized biomolecule can then be exposed to different molecules in order to identify its ligands. DNA chips and protein chips are common examples of such an approach.

Bioconjugation also allows biochemical tests, diagnostic applications by the qualitative and quantitative detection of analytes in clinical samples, applications in the field of in vivo imaging, for example by the binding of contrast agents conjugated to antibodies, and the use of immobilized enzymes used as industrial catalysts. Other less common molecules used in bioconjugation are oligosaccharides, synthetic polymers such as polyethyleneglycol (PEG), and carbon nanotubes.

The difficulty to be overcome in the bioconjugation reactions is the loss of the biological function of the target molecule due to poor control of the site where the modification takes place. The methods of bioconjugation developed recently are more specific to a site and involve minimal disturbances to the active form of the biomolecule. Moreover, certain immobilized biomolecules can exhibit an increased ligand-binding ability.

The most common chemical bioconjugation methods are based on cysteine or lysine residues. More recent methods also use synthetic functional groups, such as olefins.

The derivatization of proteins by a thiolate group of a cysteine residue is a common method of bioconjugation, as the thiolates are potential nucleophiles in an aqueous solution. Thiol-reactive functional groups include the iodoacetamides, maleimides and disulphides. By way of example, the iodoacetamides are used in a quite standard fashion in tests for determining of the presence of free cysteines in proteins. More recently, iodoacetamide groups have been used for labelling proteins with fluorophores, or for immobilizing proteins.

As the amide bonds have a high stability, they are the targets of choice for bioconjugation. For example, a protein can be treated with a small molecule or surface having an activated ester bond in order to form an amide bond with the amine groups of the lysines and the N-terminal ends. Native chemical ligation and Staudinger ligation are two recent approaches for generating amide bonds at specific sites of a given protein.

Another target for bioconjugation is the easy synthesis of carbon-nitrogen double bonds by condensation of nitrogen-containing bases with aldehydes or ketones in aqueous solutions at neutral pH. In this way oximes (C=N—O) and hydrazones (C=N—N) can be synthesized which are more stable than simple imines (C=N). Thus, the glucides are capable of being modified by carbon-nitrogen double bonds because their hydroxyl groups can be easily oxidized to aldehydes. Alternatively, ketones can be introduced onto sugars present on the surface of the cells by biosynthesis. The sugars immobilized by the oxime bonds have been used to produce sugar chips. Numerous examples of oligonucleotides conjugated by oxime or hydrazone bonds are given in the prior art. As an application, the use of peptide chips by the immobilization of peptides making it possible to detect antibodies in blood samples can be mentioned.

The Huisgen cycloaddition reaction in the presence of a copper Cu(I) catalyst is one the most used in bioconjugation. It consists of the reaction between a terminal alkyne and an azide generating a 1,4-disubstituted triazole. This reaction has been used for very many applications, in particular the labelling of proteins with small molecules, the immobilization of proteins and of peptides, applications in proteomics, the immobilization of sugars, the functionalization of DNA, and the binding of fluorescent molecules onto viruses and bioactive polymers.

In the last few years, the use of functionalized polymers with an azlactone (or oxazolone) function for the development of functional materials has increased. Due to the fact that the azlactones can react by ring opening reactions with a wide diversity of nucleophilic species, such as the primary amines, hydroxyl groups, and thiol functions, materials functionalized with an azlactone function can serve as reactive platforms for the post-synthesis or post-production introduction of a wide range of chemical functions into soluble polymers, insoluble supports and surfaces. The reactivity of this electrophilic ring is such that an opening reaction leads to the formation of a functional linker which is not very reactive. In fact, it is constituted either by two amide bonds if the nucleophile is a primary amine, or one amide bond and one ester bond if the nucleophile is an alcohol, or one amide bond and one thioester bond if the nucleophile is a thiol. They frame a highly hindered tetra-substituted centre. The overall site constituting the linker is therefore not very reactive.

The last decade has seen a significant increase in both the number and the variety of applications exploiting the properties and the reactivity of such functionalized polymers. Various studies have shown the usefulness of supports having an azlactone function such as soluble supports, films, monoliths and insoluble supports in the form of beads. The applications of these supports, related to the composition and the morphology of the support, however remain limited and mainly amount to the immobilization of enzymes, catalysts, ligands or to trapping amines.

For example, concerning the monoliths, two possible applications, in connection with their structure, have been highlighted: the hydrophilic monoliths are used in an aqueous medium in order to immobilize enzymes such as trypsine or bovine serum albumin (BSA) and the hydrophobic monoliths are used for trapping amines in an organic medium. In the same way as for the monoliths, the insoluble cross-linked supports having an azlactone functionality in the form of beads have two main applications: the immobilization of enzymes and the trapping of amines. Thus, SOLA J. et al. (Angew. Chem. Int. Ed., 2010, 49, 6836-6839) disclose azides that are used for studying modifications to the helical structures of peptidomimetic oligomers based on aminoisobutyric acid (Aib). International application WO 2004/081538 describes azlactones which are used as intermediates for the synthesis of poly (oxazolone) homopolymers capable of being conjugated with different active agents and international application WO 93/25594 describes azlactone groups fixed on supports and used for fixing the active agents.

In current therapeutic research, novel methodologies have been developed in order to more rapidly access a wide diversity of compounds. In particular, chemical ligation by "click" chemistry has been proposed by Sharpless in 2001 (H. C. Kolb, M. G. Finn and K. B. Sharpless (2001). "Click Chemistry: Diverse Chemical Function from a Few Good Reactions". *Angewandte Chemie International Edition* 40 (11): 2004-2021) in order to generate different original structures of standard pharmacophores. A reaction can be considered as a "click" reaction if it corresponds to the following criteria:

modularity
stereoselectivity
insensitivity to oxygen and to water
high purity and yield.

"Click" chemistry therefore makes it possible to develop a set of clear-cut and modular reactions which can be implemented under mild conditions, without tedious purification, without formation of by-products, having a wide spectrum of substrates which are physiologically stable and/or compatible with biological media and lead to atom economy at high yields. The main "click" reactions consist of forming very energy-efficient carbon-heteroatom bonds, in particular a ring opening nucleophilic reaction or a cycloaddition reaction. A type of reaction which is widely represented in "click" chemistry is the abovementioned alkyne-azide cycloaddition catalyzed with Cu(I). When the "click" reactions are compatible with the chemical functions and the biological media, whether in vitro or in vivo, these reactions are called bio-orthogonal.

Although numerous reagents capable of being used in these click chemistry reactions exist, a need remains for novel reagents allowing efficient and rapid reactions in an aqueous medium, without the formation of by-products which are difficult to remove and/or are toxic.

A purpose of the invention is therefore to propose a family of novel multifunctional reactive coupling agents which can be used for the combination, by covalent bonds, of biomolecules such as proteins, peptides, DNA, certain polysaccharides, with one or more other biomolecule(s), a natural or synthetic polymer, or a reactive surface. These novel compounds are of quite particular interest for "click" chemistry applied to biology and chemical synthesis.

Another purpose of the invention is also to overcome the drawbacks of the state of the art by proposing novel coupling reagents:

allowing combinations by bio-orthogonal methods, both in vitro and in vivo, the reactive functionalities of which are also orthogonal between themselves, the high reactivity of which is compatible with biological media, having a resistance to hydrolysis in an aqueous medium, without the formation of by-products which are toxic or difficult to remove, applicable to a wide range of biological or synthetic macromolecules, leading to chemical bonds which are robust and compatible with a vast range of chemical functionalities as well as with biological media and living organisms, in vitro and in vivo.

Certain compounds corresponding to general formula (I)

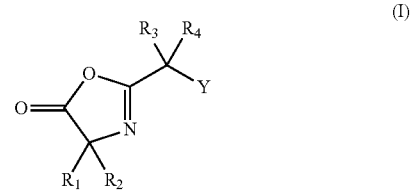

in which $R_1$ and $R_2$ represent independently of one another a $(C_1$-$C_{10})$alkyl group, a $(C_2$-$C_6)$cycloalkyl group, an aryl group, an aryl$(C_1$-$C_{10})$alkyl group, or a heterocyclic group, $R_3$ and $R_4$ represent independently of one another a hydrogen atom, a $(C_1$-$C_{10})$alkyl group, an aryl group or an aryl$(C_1$-$C_{10})$alkyl group, and Y represents a reactive function which can be activated by click chemistry, selected from the group comprising the azides, alkynes, cycloalkynes and conjugated dienes, are known as such but are not described as multifunctional coupling reactive agents (see SOLA J. cited previously).

According to the present invention, the term "$(C_1$-$C_{10})$alkyl" represents a linear or branched, saturated hydrocarbon-containing group, having 1 to 10 carbon atoms, advantageously from 1 to 5 carbon atoms. By way of example, the methyl, ethyl, propyl, isopropyl, butyl, isobutyl, sec-butyl, tertiobutyl, pentyl, neopentyl, isopentyl, tert-pentyl, hexyl, isohexyl, heptyl, octyl, nonyl and decyl groups can be mentioned.

The term "aryl" represents a mono- or bicyclic, aromatic hydrocarbon-containing group comprising from 6 to 10 carbon atoms. By way of example the phenyl and naphthyl groups can be mentioned.

By the term "aryl$(C_1$-$C_{10})$alkyl", is meant an alkyl group having 1 to 10 carbon atoms, advantageously from 1 to 5 carbon atoms as defined previously and containing an aryl group as defined above.

The term "heterocyclic group" represents any saturated or unsaturated heterocycle, comprising from 3 to 7 carbon atoms and containing 1 to 3 heteroatoms selected from the group constituted by oxygen, nitrogen or sulphur. For example, the piperidinyl, pyrrolidinyl, piperazinyl, pyridyl, piridinyl, imidazolyl, furyl, morpholinyl, oxetanyl, tetrahydrofuranyl, tetrahydropyranyl, tetrahydrothienyl, and thiazolyl groups can be mentioned.

The term "azides" represents the salts of hydrozoic acid $HN_3$, as well as the organic azides in which one of the nitrogen atoms is covalently bound to a carbon atom of an organic compound. As examples methyl azide and phenyl azide can be mentioned.

The term "alkynes" represents hydrocarbons having an unsaturation characterized by the presence of a triple carbon-carbon bond. As examples ethyne, propyne, but-1-yne, and but-2-yne can be mentioned.

By "cycloalkynes" is meant any ring of carbon atoms containing one or more triples bonds, such as cyclooctyne.

The term "conjugated dienes" represents hydrocarbons having two double bonds separated by one single bond. By way of example, butadiene, isoprene, 2,3-dimethyl-1,3-butadiene, 1,3-pentadiene, 2-phenyl-1,3-butadiene and furan can be mentioned.

The first chemical function common to the compounds corresponding to formula (I) used according to the invention is of azlactone (2-oxazolin-5-one) type. This group is known for reacting by ring opening with primary amine functions without requiring a catalyst and with the formation of a robust amide bond under mild conditions, in particular in an aqueous solution, therefore compatible with biological media. The major use of this chemical function compared to the systems already described resides, in addition to its intrinsic reactivity leading to a rapid and efficient reaction in an aqueous medium due to its resistance to hydrolysis, in the fact that the reaction with an amine does not lead to the formation of reaction by-products which are possibly toxic and difficult to remove from the reaction medium. The primary amine functions are widespread in most biological molecules (proteins, nucleic acids in particular) and molecules of biological interest, which ensures a very broad field of application for the reagents of this invention. In terms of cost, the absence of by-products generated by the reaction of the azlactone group also leads to atom economy. Moreover, the possibility of working in an aqueous medium is an advantage in terms of the environment.

The other common function present in the compounds corresponding to formula (I) used according to the invention corresponds to a group capable of participating in a cycloaddition reaction, in particular the azide, alkyne, cycloalkyne and conjugated diene groups. The cycloaddition reactions constitute the most widespread examples of click chemistry, in particular the Huisgen reaction mentioned previously, [4+2] cycloaddition (Diels-Alder reaction), and heterocycloaddition. These reactions are bio-orthogonal, i.e. they are compatible with the species present in biological media. In fact, they utilize functional groups which are in general neither present, nor capable of reacting with the groups which exist within the biomolecules.

The two chemical functions present in the compounds according to the invention are moreover orthogonal between themselves, i.e. they react under different conditions, independently of one another. It is therefore possible to trigger the reaction of one of these two groups without the other being converted, thus allowing successive chemoselective reactions.

A subject of the present invention is compounds of formula (I)

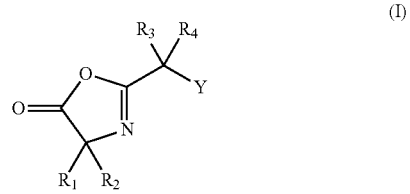

(I)

in which $R_1$ and $R_2$ represent independently of one another a $(C_1-C_{10})$alkyl group, a $(C_2-C_6)$cycloalkyl group, an aryl group, an aryl$(C_1-C_{10})$alkyl group, or a heterocyclic group, $R_3$ and $R_4$ represent independently of one another a hydrogen atom, a $(C_1-C_{10})$alkyl group, an aryl group or an aryl$(C_1-C_{10})$alkyl group, and Y represents:
(i) an $N_3$ group, or
(ii) a $(C_1-C_{10})$alkyl-$N_3$ group, or
(iii) an aryl-$N_3$ group, or
(iv) an aryl$(C_1-C_{10})$alkyl-$N_3$ group, or
(v) a $(C_1-C_{10})$alkyl-C≡C—$R_5$ group, or
(vi) an aryl-C≡C—$R_5$ group, or
(vii) an aryl$(C_1-C_{10})$alkyl-C≡C—$R_5$ group, or
(viii) an —O—C(O)—$(CH_2)_n$—C≡$CR_5$ group, with n an integer comprised between 1 and 10, in particular an —O—C(O)—$(CH_2)_n$—C≡CH group, with n comprised between 1 and 5, with $R_5$ representing
(a) either a hydrogen atom,
(b) or a $(C_1-C_{10})$alkyl group,
(c) or an aryl group,
(d) or an aryl$(C_1-C_{10})$alkyl group,
all these groups being able to contain two conjugated double bonds, optionally in a ring,
(e) or a protective group of the triple bond.

In the definitions (i) to (viii), the terms $(C_1-C_{10})$alkyl, aryl and aryl$(C_1-C_{10})$alkyl refer to the definitions given previously.

As examples of a $(C_1-C_{10})$alkyl, aryl or aryl$(C_1-C_{10})$alkyl group, capable of containing two conjugated double bonds, optionally in a ring, in particular 1,3-butadienyl, cyclopentadienyl, pyrrolyl and furyl can be mentioned.

All the groups mentioned have in common the ability to produce a [3+2] dipolar cycloaddition or a cycloaddition or a [4+2] heterocycloaddition reaction.

The protective groups of the triple bond are well known to a person skilled in the art. As examples, the trialkysilyls, in particular trimethylsilyl, triethylsilyl, tert-butyldimethylsilyl and benzyldimethylsilyl can be mentioned.

According to another advantageous embodiment of the invention, the compounds of formula (I) are those for which $R_1$ and $R_2$ each represent a $(C_1-C_{10})$alkyl group, $R_3$ represents a hydrogen atom, $R_4$ represents a methyl group, and Y represents either an $N_3$ group, or an —O—C(O)—$(CH_2)_3$—C≡CH group.

Advantageously, the $R_1$, $R_2$ and $R_4$ groups each represent a methyl group, $R_3$ a hydrogen atom and Y an $N_3$ group.

According to another advantageous embodiment of the invention, $R_1$, $R_2$ and $R_4$ each refer to a methyl group, $R_3$ a hydrogen atom and Y an —O—C(O)—$(CH_2)_3$—C≡CH group.

Another subject of the invention is a method for coupling a biomolecule and a target molecule selected from the group comprising a molecule of biological interest, a natural or synthetic polymer, and a reactive surface, said method utilizing a compound of formula (I) in which $R_1$ and $R_2$ represent independently of one another a $(C_1-C_{10})$alkyl group, a $(C_2-C_6)$cycloalkyl group, an aryl group, an aryl$(C_1-C_{10})$alkyl group, or a heterocyclic group, $R_3$ and $R_4$ represent independently of one another a hydrogen atom, a $(C_1-C_{10})$alkyl group, an aryl group or an aryl$(C_1-C_{10})$alkyl group, and Y represents a reactive function which can be activated by click chemistry, selected from the group comprising the azides, alkynes, cycloalkynes and conjugated dienes, and comprising the following steps:
bringing said compound of formula (I) into contact with a biomolecule,
bringing said compound of formula (I) bound to the biomolecule into contact with the target molecule and if necessary,
isolating the coupling product.

In an advantageous embodiment of the invention, the coupling method utilizes a compound of formula (I) in which $R_1$ and $R_2$ represent independently of one another a $(C_1-C_{10})$alkyl group, a $(C_2-C_6)$cycloalkyl group, an aryl group, an aryl$(C_1-C_{10})$alkyl group, or a heterocyclic group, $R_3$ and $R_4$ represent independently of one another a hydrogen atom, a $(C_1-C_{10})$alkyl group, an aryl group or an aryl$(C_1-C_{10})$alkyl group, and Y represents:
(i) an $N_3$ group, or
(ii) a $(C_1-C_{10})$alkyl-$N_3$ group, or
(iii) an aryl-$N_3$ group, or
(iv) an aryl$(C_1-C_{10})$alkyl-$N_3$ group, or
(v) a $(C_1-C_{10})$alkyl-C≡C—$R_5$ group, or
(vi) an aryl-C≡C—$R_5$ group, or
(vii) an aryl$(C_1-C_{10})$alkyl-C≡C—$R_5$ group, or
(viii) an —O—C(O)—$(CH_2)_n$—C≡C$R_5$ group, with n an integer comprised between 1 and 10, in particular an —O—C(O)—$(CH_2)_n$—C≡CH group, with n comprised between 1 and 5,
with $R_5$ representing
  (a) either a hydrogen atom,
  (b) or a $(C_1-C_{10})$alkyl group,
  (c) or an aryl group,
  (d) or an aryl$(C_1-C_{10})$alkyl group,
  all these groups being able to contain two conjugated double bonds, optionally in a ring,
  (e) or a protective group of the triple bond.

By "reactive surface", is meant an organic or inorganic material having chemical functions on its surface capable of reacting with the molecules of the present invention. For example, a surface (film, fabric, etc.) of polypropylene or polyethylene having amine functions on the surface can be mentioned.

According to an advantageous embodiment of the method according to the invention, the biomolecule(s) involved in said coupling method are selected from the group comprising proteins, peptides, DNA, biological markers, hormones, vitamins, antibodies, polyamines, monosaccharides, oligosaccharides and polysaccharides, and the molecules of biological interest of medicinal type such as anticancers, anti-virals, or labels such as fluorescent or radioactive labels.

Another subject of the invention is a diagnostic reagent utilizing at least one compound of formula (I), in particular a compound for which $R_1$ and $R_2$ represent independently of one another a $(C_1-C_{10})$alkyl group, a $(C_2-C_6)$cycloalkyl group, an aryl group, an aryl$(C_1-C_{10})$alkyl group, or a heterocyclic group, $R_3$ and $R_4$ represent independently of one another a hydrogen atom, a $(C_1-C_{10})$alkyl group, an aryl group or an aryl$(C_1-C_{10})$alkyl group, and Y represents:
(i) an $N_3$ group, or
(ii) a $(C_1-C_{10})$alkyl-$N_3$ group, or
(iii) an aryl-$N_3$ group, or
(iv) an aryl$(C_1-C_{10})$alkyl-$N_3$ group, or
(v) a $(C_1-C_{10})$alkyl-C≡C—$R_5$ group, or
(vi) an aryl-C≡C—$R_5$ group, or
(vii) an aryl$(C_1-C_{10})$alkyl-C≡C—$R_5$ group, or
(viii) an —O—C(O)—$(CH_2)_n$—C≡C$R_5$ group, with n an integer comprised between 1 and 10, in particular a —O—C(O)—$(CH_2)_n$—C≡CH group, with n comprised between 1 and 5,
with $R_5$ representing
  (a) either a hydrogen atom,
  (b) or a $(C_1-C_{10})$alkyl group,
  (c) or an aryl group,
  (d) or an aryl$(C_1-C_{10})$alkyl group,
  all these groups being able to contain two conjugated double bonds, optionally in a ring,
  (e) or a protective group of the triple bond.

A subject of the invention is also the use of the compounds of formula (I) in which $R_1$ and $R_2$ represent independently of one another a $(C_1-C_{10})$alkyl group, a $(C_2-C_6)$cycloalkyl group, an aryl group, an aryl$(C_1-C_{10})$alkyl group, or a heterocyclic group, $R_3$ and $R_4$ represent independently of one another a hydrogen atom, a $(C_1-C_{10})$alkyl group, an aryl group or an aryl$(C_1-C_{10})$alkyl group, and Y represents a reactive function which can be activated by click chemistry, selected from the group comprising the azides, alkynes, cycloalkynes and conjugated dienes, as a diagnostic reagent and a diagnostic method utilizing the set of the compounds of formula (I).

In fact, the coupling agents are of use in the field of diagnostics, in particular in the detection of reactions of the ligand-anti-ligand type such as antigen-antibody or protein-protein, as they make it possible to directly couple a molecule of biological interest, such as an antigen, to a molecule called a development molecule, such as an enzyme. The bond of the biological molecule of interest to another molecule, such as an antibody, is demonstrated due to the development molecule. It can be also useful for coupling a fluorescent probe to a molecule of biological interest for its detection by functional imaging.

Another subject of the invention is a kit for the implementation of a coupling and bioconjugation method comprising at least one compound of formula (I), in particular those for which $R_1$ and $R_2$ represent independently of one another a $(C_1-C_{10})$alkyl group, a $(C_2-C_6)$cycloalkyl group, an aryl group, an aryl$(C_1-C_{10})$alkyl group, or a heterocyclic group, $R_3$ and $R_4$ represent independently of one another a hydrogen atom, a $(C_1-C_{10})$alkyl group, an aryl group or an aryl$(C_1-C_{10})$alkyl group, and Y represents:
(i) an $N_3$ group, or
(ii) a $(C_1-C_{10})$alkyl-$N_3$ group, or
(iii) an aryl-$N_3$ group, or
(iv) an aryl$(C_1-C_{10})$alkyl-$N_3$ group, or
(v) a $(C_1-C_{10})$alkyl-C≡C—$R_5$ group, or
(vi) an aryl-C≡C—$R_5$ group, or
(vii) an aryl$(C_1-C_{10})$alkyl-C≡C—$R_5$ group, or
(viii) an —O—C(O)—$(CH_2)_n$—C≡C$R_5$ group, with n an integer comprised between 1 and 10, in particular a —O—C(O)—$(CH_2)_n$—C≡CH group, with n comprised between 1 and 5,
with $R_5$ representing
  (a) either a hydrogen atom,
  (b) or a $(C_1-C_{10})$alkyl group,
  (c) or an aryl group,
  (d) or an aryl$(C_1-C_{10})$alkyl group,
  all these groups being able to contain two conjugated double bonds, optionally in a ring,
  (e) or a protective group of the triple bond.

Another subject of the invention is a method for the separation, detection and/or characterization of at least one molecule of interest potentially present in a medium, comprising at least one step of utilizing a kit according to the invention or at least one compound of formula (I) in which $R_1$ and $R_2$ represent independently of one another a $(C_1$-$C_{10})$alkyl group, a $(C_2$-$C_6)$cycloalkyl group, an aryl group, an aryl$(C_1$-$C_{10})$alkyl group, or a heterocyclic group, $R_3$ and $R_4$ represent independently of one another a hydrogen atom, a $(C_1$-$C_{10})$alkyl group, an aryl group or an aryl$(C_1$-$C_{10})$alkyl group, and Y represents a reactive function which can be activated by click chemistry, selected from the group comprising the azides, alkynes, cycloalkynes and conjugated dienes.

Another subject of the invention is a composition comprising a compound of formula (I) in which $R_1$ and $R_2$ represent independently of one another a $(C_1$-$C_{10})$alkyl group, a $(C_2$-$C_6)$cycloalkyl group, an aryl group, an aryl$(C_1$-$C_{10})$alkyl group, or a heterocyclic group, $R_3$ and $R_4$ represent independently of one another a hydrogen atom, a $(C_1$-$C_{10})$alkyl group, an aryl group or an aryl$(C_1$-$C_{10})$alkyl group, and Y represents:

(i) an $N_3$ group, or (ii) a $(C_1$-$C_{10})$alkyl-$N_3$ group, or (iii) an aryl-$N_3$ group, or (iv) an aryl$(C_1$-$C_{10})$alkyl-$N_3$ group, or (v) a $(C_1$-$C_{10})$alkyl-C≡C—$R_5$ group, or (vi) an aryl-C≡C—$R_5$ group, or (vii) an aryl$(C_1$-$C_{10})$alkyl-C≡C—$R_5$ group, or (viii) an —O—C(O)—$(CH_2)_n$—C≡C$R_5$ group, with n an integer comprised between 1 and 10, in particular an —O—C(O)—$(CH_2)_n$—C≡CH group, with n comprised between 1 and 5, with $R_5$ representing (a) either a hydrogen atom, (b) or a $(C_1$-$C_{10})$alkyl group, (c) or an aryl group, (d) or an aryl$(C_1$-$C_{10})$alkyl group, all these groups being able to contain two conjugated double bonds, optionally in a ring, (e) or a protective group of the triple bond in combination with an aqueous or organic medium.

As organic medium, for example dimethylsulphoxide (DMSO) compatible with the cell cultures can be mentioned.

The invention is illustrated by Examples 1 to 6 and FIG. 1 which follow.

Examples 1, 2 and 4, 5 illustrate the synthesis of compounds according to the invention and Examples 3 and 6 the method for coupling a compound of the invention and a biomolecule: lysozyme.

FIG. 1 represents the MALDI-TOF analysis spectrum of the lysozyme-2-(1-azidoethyl)-4,4-dimethyloxazol-5(4H)-one conjugate obtained according to the coupling method described in Example 3.

EXAMPLE 1

2-(1-azidoethyl)-4,4-dimethyloxazol-5(4H)-one 2-(1-azidoethyl)-4,4-dimethyloxazol-5(4H)-one is prepared according to Diagram 1 below.

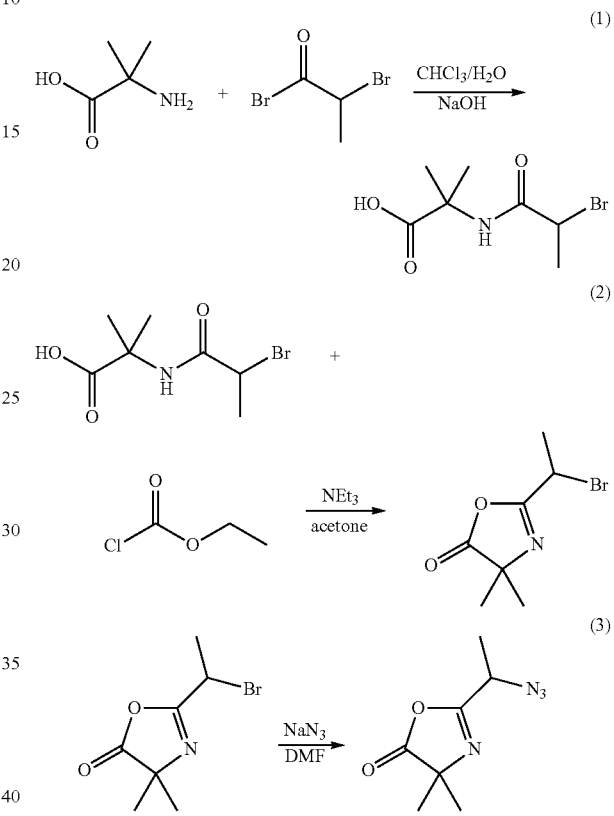

Diagram 1

1.1.
2-(1-bromoethyl)-4,4-dimethyloxazol-5(4H)-one

This synthesis intermediate is prepared according to the procedure described by K. M. Lewandowski et al. in the U.S. Pat. No. 6,762,257 B1 (steps 1 and 2 of Diagram 1)

1.2. 2-(1-azidoethyl)-4,4-dimethyloxazol-5(4H)-one 2-(1-azidoethyl)-4,4-dimethyloxazol-5(4H)-one is then obtained (step 3) according to the protocol below.

In a 25-mL flask equipped with a magnetic stirrer, under an argon atmosphere, a solution of 0.65 g (0.01 mol) of sodium azide in 4 mL of anhydrous dimethylformamide (DMF) is prepared, which is cooled down using an ice bath. A solution comprising 2.20 g, (0.01 mol) of 2-(1-bromoethyl)-4,4-dimethyloxazol-5(4H)-one, prepared in step 1.1., in 2 mL of anhydrous DMF is poured dropwise into this mixture and left under stirring at 0° C. for 2 h. The mixture is left to return to ambient temperature under stirring for 24 h. The solvent is evaporated off under reduced pressure and the residue is taken up in ethyl acetate then the solution is filtered in order to remove the sodium bromide. The filtrate is poured into a separating funnel and the solution is washed with dilute HCl (5%) then saturated aqueous $NaHCO_3$. The organic phase is dried over $MgSO_4$, filtered and concentrated under vacuum. The yellow oil obtained is purified by silica column chromatography with, successively n-hexane, then an n-hexane:ethyl acetate mixture 8:2 v/v, in order to produce an oil (0.57 g, 31%) which crystallizes when cold.

The 2-(1-azidoethyl)-4,4-dimethyloxazol-5(4H)-one is characterized by proton nuclear magnetic resonance ($^1$H NMR) and by carbon 13 nuclear magnetic resonance ($^{13}$C NMR).

$^1$H NMR (400 MHz, $CDCl_3$, δ ppm): 1.46 ppm (s, 6H, —C(CH$_3$)$_2$), 1.56 ppm (d, 3H, —CH(CH$_3$)N$_3$), 4.27 ppm (t, 1H, CH(CH$_3$)N$_3$).

$^{13}$C NMR (400 MHz, $CDCl_3$, δ ppm): 16.32 ppm (—C(CH$_3$)N$_3$), 24.46 ppm (C(CH$_3$)$_2$), 53.76 ppm (—C(CH$_3$)N$_3$), 65.59 ppm (—C(CH$_3$)$_2$), 161.56 ppm (C═N), 180.11 ppm (C═O).

EXAMPLE 2

1-(4,4-dimethyl-5-oxo-4,5-dihydrooxazol-2-yl)ethyl hex-5-ynoate 1-(4,4-dimethyl-5-oxo-4,5-dihydrooxazol-2-yl)ethyl hex-5-ynoate is prepared according to Diagram 2 below.

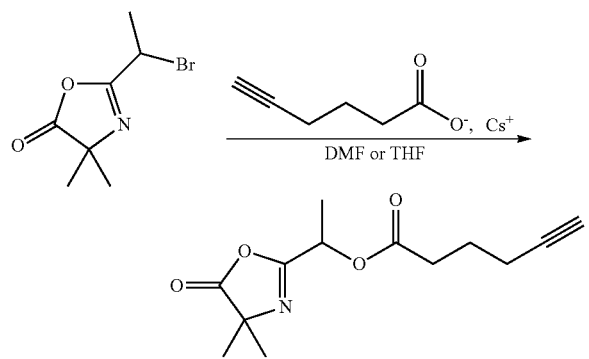

2-(1-bromoethyl)-4,4-dimethyloxazol-5(4H)-one is prepared according to Example 1.1.

2.2 1-(4,4-dimethyl-5-oxo-4,5-dihydrooxazol-2-yl)ethyl hex-5-ynoate

2.2.1. Caesium salt of 5-hexynoic acid 5-hexynoic acid is prepared by reaction of caesium carbonate (4.10 g, 0.0126 mol) with 5-hexynoic acid (4.6 g, 0.0411 mol) in solution in DMF (6.0 mL) at ambient temperature for 16 h. The reaction mixture is filtered, the solvent is removed under reduced pressure and the residue taken up in diethyl ether. After filtration, the caesium salt of 5-hexynoic acid (4.82 g, yield 78%) is dried under vacuum at 40° C.

2.2.2. 1-(4,4-dimethyl-5-oxo-4,5-dihydrooxazol-2-yl)ethyl hex-5-ynoate

A solution of 2-(1-bromoethyl)-4,4-dimethyloxazol-5 (4H)-one (0.448 g, 2.03 mmol) in DMF (2 mL) is added dropwise to a solution of caesium salt of 5-hexynoic acid (0.490 g, 2 mmol) in anhydrous DMF (3 mL) placed in a flask cooled down with an ice bath. At the end of the addition, the reaction mixture is left under stirring at 0° C. for 2 h then left to return to ambient temperature over 24 h. The solvent is removed under reduced pressure then the residue is taken up in ethyl acetate, filtered and concentrated under vacuum. The yellow oil obtained is purified by silica column chromatography in order to produce 0.310 g (61%) of 1-(4,4-dimethyl-5-oxo-4,5-dihydrooxazol-2-yl)ethyl hex-5-ynoate.

The 1-(4,4-dimethyl-5-oxo-4,5-dihydrooxazol-2-yl)ethyl hex-5-ynoate is characterized by proton nuclear magnetic resonance ($^1$H NMR) and by carbon 13 nuclear magnetic resonance ($^{13}$C NMR).

$^1$H NMR (400 MHz, $CDCl_3$, δ ppm): 1.46 ppm (s, 6H, —C(CH$_3$)$_2$), 1.56 ppm (d, 3H, —CH(CH$_3$)OCO), 1.85 ppm (quinquet, 2H, HC≡C—CH$_2$CH$_2$CH$_2$—O—CO—), 2.00 ppm (HC≡C—), 2.29 ppm (triplet-doublet, HC≡C—CH$_2$CH$_2$CH$_2$—O—CO—), 2.54 ppm (HC≡C—CH$_2$CH$_2$CH$_2$—O—CO—), 5.57 ppm (quadruplet, 1H, —CH$_2$—COOCH(CH$_3$)—).

$^{13}$C NMR (400 MHz, $CDCl_3$, δ ppm): 17.01 ppm (—CH$_2$—COOCH(CH$_3$)), 17.75 ppm (HC≡C—CH$_2$—), 23.50 ppm (HC≡C—CH$_2$CH$_2$CH$_2$—), 24.42 ppm (C(CH$_3$)$_2$), 32.62 ppm (—CH$_2$CH$_2$CO)—), 65.04 ppm (C(CH$_3$)$_2$), 65.45 ppm (HC≡C—CH$_2$—), 69.50 ppm (—COO—CH(CH$_3$)—), 83.24 ppm (HC≡C—CH$_2$—), 162.06 ppm (C═N), 172.26 ppm (—CH$_2$—COO—CH(CH$_3$)—), 180.52 ppm (C═O)$_{ring}$.

EXAMPLE 3

Process for coupling 2-(1-azidoethyl)-4,4-dimethyloxazol-5(4H)-one with lysozyme The coupling of a model protein, lysozyme, with 2-(1-azidoethyl)-4,4-dimethyloxazol-5(4H)-one is described below:

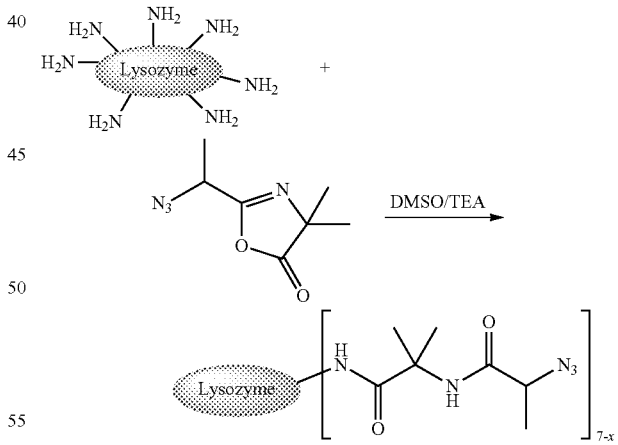

3.1. Procedure

In a flask equipped with a magnetic stirrer, a solution of lysozyme (114.2 mg, $8.0 \times 10^{-6}$ mol) in dimethylsulphoxide (DMSO, 10.00 mL) is prepared, to which trimethylamine (TEA, 0.20 mL, $1.49 \times 10^{-3}$ mol) is added. After stirring for 15 minutes at ambient temperature, a solution of 2-(1-azidoethyl)-4,4-dimethyloxazol-5(4H)-one prepared according to Example 1 (0.252 g, $1.38 \times 10^{-3}$ mol) in DMSO (1.00 mL) is added and the reaction mixture is left under stirring at ambient temperature for 24 h. After 24 h, an aqueous solution of HCl (HCl, 37%, 1.0 mL per 30.0 mL of solution) is added then the solution is dialyzed with a dialysis membrane (cut-off threshold=MWCO=3500) against an aqueous solution of methanol (water:methanol=8:2 in volumes) for 24 h. The product is then recovered by lyophilization. The final product (0.012 g) is dissolved in DMSO (0.10 mL) for analysis by Fourier Transform infrared (FTIR) spectroscopy. Analysis by time-of-flight mass spectrometry (MALDI-TOF MS) is also carried out.

3.2. Results

The FTIR spectrum of the sample shows the presence of a new absorption band at 2110 cm$^{-1}$, characteristic of the azide group introduced onto the protein.

The reaction is also attested by time-of-flight mass spectrometry (MALDI-TOF MS) which shows that after reaction the initial lysozyme peak at m/z=14357 has disappeared in favour of a new signal centred at m/z=15812 (FIG. 1).

EXAMPLE 4

Synthesis of 1-(4,4-dimethyl-5-oxo-4,5-dihydro oxazol-2-yl)ethyl hexa-2,4-dienoate 1-(4,4-dimethyl-5-oxo-4,5-dihydrooxazol-2-yl)ethyl-hexa-2,4-dienoate is prepared according to the diagram below:

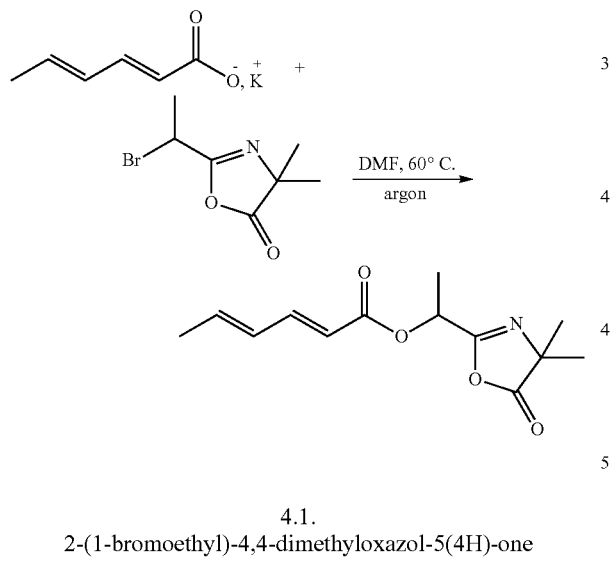

4.1.
2-(1-bromoethyl)-4,4-dimethyloxazol-5(4H)-one

This is prepared according to the procedure described by K. M. Lewandowski et al. in the U.S. Pat. No. 6,762,257 B1 (2004).

4.2. 1-(4,4-dimethyl-5-oxo-4,5-dihydrooxazol-2-yl) ethylhexa-2,4-dienoate

Potassium sorbate (1.12 g, 7.5×10$^{-3}$ mol), 2-(1-bromoethyl)-4,4-dimethyloxazol-5(4H)-one (1.68 g, 7.6×10$^{-3}$ mol) and anhydrous DMF (20.0 mL) are introduced into a flask equipped with a magnetic stirrer. Then, the reaction mixture is stirred and heated at 60° C. under argon for 17 h. The solvent (DMF) is removed under reduced pressure. The residue is taken up in acetone then filtered on frit. The filtrate obtained is concentrated under vacuum. The final product is obtained in the form of a dark yellow oil with a yield of 95% (1.90 g) which crystallizes when cold.

$^1$H NMR (400 MHz, acetone D$_6$, δ ppm): 1.40 ppm (6H, —C(CH$_3$)$_2$), 1.59 ppm (d, 3H, —COOCH(CH$_3$)), 1.90 ppm (d, 3H, H$_3$C—CH$_2$=CH$_2$—), 5.63 ppm (q, 1H, —CH(CH$_3$) OCO), 5.91 (d, 1H, CH$_3$—CH=CH—CH=CH—), 6.34 ppm (CH$_3$—CH=CH—CH=CH—), 7.34 ppm (1H, CH$_3$—CH=CH—CH=CH—).

$^{13}$C NMR (400 MHz, acetone D$_6$, δ ppm): 17.01 ppm (—COOCH(CH$_3$)—), 18.51 ppm (H$_3$C—CH$_2$=CH$_2$—), 24.21 ppm and 24.31 ppm (C(CH$_3$)$_2$), 65.04 ppm (C(CH$_3$)$_2$), 65.85 ppm (—COO—CH(CH$_3$)—), 118.47 (CH$_3$—CH=CH—CH=CH—), 130.31 (CH$_3$—CH=CH—CH=CH—), 141.03 ppm (CH$_3$—CH=CH—CH=CH—), 146.88 ppm (CH$_3$—CH=CH—CH=CH—), 162.21 ppm (C=N), 165.92 ppm (—COO—CH(CH$_3$)—), 181.16 ppm (C=O)$_{ring}$.

HR-MS: C$_{13}$H$_{17}$NO$_4$ m/z=[M+H]$_{exp}$=252.1239 ([M+H]$_{cal}$=252.1236).

FT-IR: ν(CH)=2985-2939, ν(C=O)azlactone=1826 cm$^{-1}$, ν(C=O)ester=1720 cm$^{-1}$, ν(C=N)=1683 cm$^{-1}$.

EXAMPLE 5

Synthesis of 2-(2-azidopropan-2-yl)-4,4-dimethyl-oxazol-5(4H)-one 2-(2-azidopropan-2-yl)-4,4-dimethyloxazol-5(4H)-one is synthesized according to the diagram below:

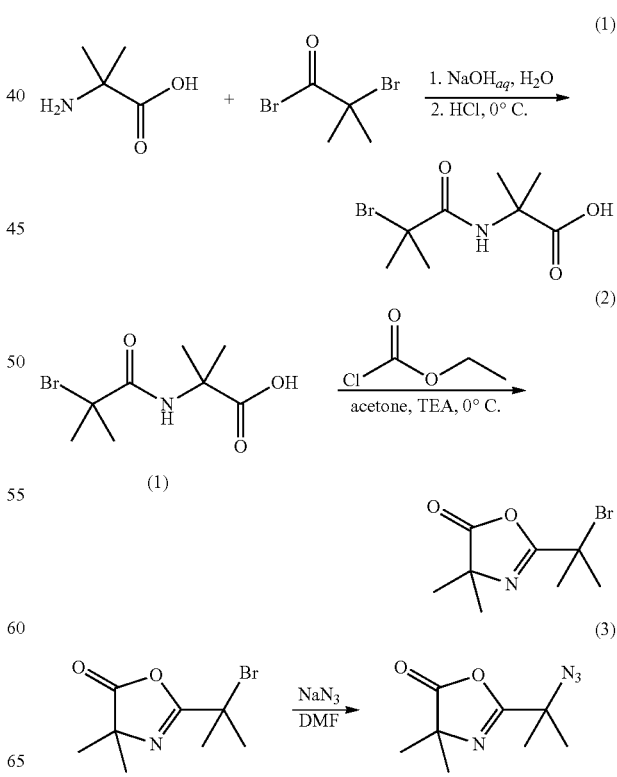

5.1. 2-(2-bromopropan-2-yl)-4,4-dimethyloxazol-5(4H)-one

This intermediate is prepared according to the procedure described by K. M. Lewandowski et al. in the U.S. Pat. No. 6,894,133 (steps 1 and 2)

5.2. 2-(2-azidopropan-2-yl)-4,4-dimethyloxazol-5(4H)-one

It is obtained (step 3) according to the following procedure:

In a 25-mL flask equipped with a magnetic stirrer, under an argon atmosphere, a solution of 0.65 g (0.01 mol) of sodium azide in 5 mL of anhydrous DMF is prepared, which is cooled down using an ice bath. A solution comprising 2.34 g, (0.01 mol) of 2-(2-bromopropan-2-yl)-4,4-dimethyloxazol-5(4H)-one in 2 mL of anhydrous DMF is poured dropwise into this mixture. The reaction mixture is stirred at 0° C. for 2 h then at ambient temperature for 16 h. The solvent is evaporated off under reduced pressure. The residue is taken up in ethyl acetate then the solution is filtered in order to remove the sodium bromide. The filtrate obtained is concentrated under vacuum. The yellow oil obtained is purified by silica column chromatography with, successively, n-hexane then an n-hexane:ethyl acetate mixture 6:4 v/v in order to produce a colourless oil (0.84 g, 43%).

$^1$H NMR (200 MHz, CDCl$_3$, δ ppm): 1.44 ppm (s, 6H, —C(CH$_3$)$_2$), 1.56 ppm (s, 6H, N$_3$C(CH$_3$)$_2$).

$^{13}$C NMR (400 MHz, CDCl$_3$, δ ppm): 24.01 ppm (N$_3$C (CH$_3$)$_2$), 24.58 ppm (—C(CH$_3$)$_2$), 59.26 ppm (N$_3$C(CH$_3$)$_2$), 65.83 ppm (—C(CH$_3$)$_2$), 163.88 ppm (C=N), 180.41 ppm (C=O).

EXAMPLE 6

Process for coupling 1-(4,4-dimethyl-5-oxo-4,5-dihydrooxazol-2-yl)ethyl hex-5-ynoate with lysozyme In a flask equipped with a magnetic stirrer, a solution of lysozyme (228.4 mg, 16.0×10$^{-6}$ mol) in dimethylsulphoxide (DMSO, 20.00 mL) is prepared, to which triethylamine (TEA, 0.30 g, 3.0×10$^{-3}$ mol) is added. After stirring for 30 min at ambient temperature, a solution of 1-(4,4-dimethyl-5-oxo-4,5-dihydrooxazol-2-yl)ethyl hex-5-ynoate (0.695 g, 3.0×10$^{-3}$ mol) in DMSO (4.00 mL) is added and the reaction mixture is stirred at ambient temperature for 24 h. After 24 h, a mixture of concentrated HCl (37%, 2 mL) and 90 mL of pure water is added, then the solution is dialyzed with a dialysis membrane (cut-off threshold=MWCO=3500) against an aqueous solution of methanol (water:methanol=8:2 in volumes) for 24 h. The product is then recovered by lyophilization.

The final product is analyzed by time-of-flight mass spectrometry (MALDI-TOF MS). The MALDI-TOF analysis result shows that after the reaction the initial lysozyme peak at m/z=14357 has disappeared in favour of a new signal centred at m/z=17819.

The invention claimed is:

1. Compound corresponding to general formula (I)

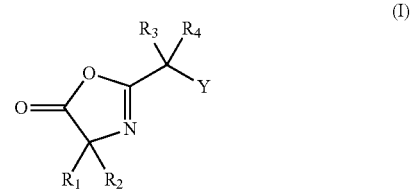

in which
R$_1$ and R$_2$ represent independently of one another a (C$_1$-C$_{10}$)alkyl group, a (C$_2$-C$_6$)cycloalkyl group, an aryl group, an aryl(C$_1$-C$_{10}$)alkyl group, or a heterocyclic group,
R$_3$ and R$_4$ represent independently of one another a hydrogen atom, a (C$_1$-C$_{10}$)alkyl group, an aryl group or an aryl(C$_1$-C$_{10}$)alkyl group, and
Y represents:
(i) an N$_3$ group, or
(ii) a (C$_1$-C$_{10}$)alkyl-N$_3$ group, or
(iii) an aryl-N$_3$ group, or
(iv) an aryl(C$_1$-C$_{10}$)alkyl-N$_3$ group, or
(v) a (C$_1$-C$_{10}$)alkyl-C≡C—R$_5$ group, or
(vi) an aryl-C≡C—R$_5$ group, or
(vii) an aryl(C$_1$-C$_{10}$)alkyl-C≡C—R$_5$ group, or
(viii) an —O—C(O)—(CH$_2$)$_n$—C≡CR$_5$ group, with n an integer comprised between 1 and 10, in particular a —O—C(O)—(CH$_2$)$_n$—C≡CH group, with n comprised between 1 and 5,
with R$_5$ representing
(a) either a hydrogen atom,
(b) or a (C$_1$-C$_{10}$)alkyl group,
(c) or an aryl group,
(d) or an aryl(C$_1$-C$_{10}$)alkyl group,
all these groups being able to contain two conjugated double bonds, optionally in a ring,
(e) or a protective group of the triple bond.

2. Compound according to claim 1 in which R$_1$ and R$_2$ each represent a (C$_1$-C$_{10}$)alkyl group, R$_3$ represents a hydrogen atom, R$_4$ represents a methyl group, and Y represents either an N$_3$ group, or an —O—C(O)—(CH$_2$)$_3$—C≡CH group.

3. Compound according to claim 2 in which R$_1$, R$_2$ and R$_4$ each represent a methyl group, R$_3$ a hydrogen atom and Y an N$_3$ group.

4. Compound according to claim 2 in which R$_1$, R$_2$ and R$_4$ each denote a methyl group, R$_3$ a hydrogen atom and Y an —O—C(O)—(CH$_2$)$_3$—C≡CH group.

5. Method for coupling a biomolecule and a target molecule selected from the group comprising a molecule of biological interest, a natural or synthetic polymer, and a reactive surface, characterized in that it utilizes a compound of formula (I)

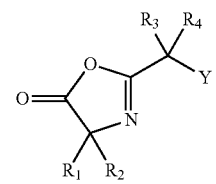

in which
- $R_1$ and $R_2$ represent independently of one another a $(C_1\text{-}C_{10})$alkyl group, a $(C_2\text{-}C_6)$cycloalkyl group, an aryl group, an aryl$(C_1\text{-}C_{10})$alkyl group, or a heterocyclic group,
- $R_3$ and $R_4$ represent independently of one another a hydrogen atom, a $(C_1\text{-}C_{10})$alkyl group, an aryl group or an aryl$(C_1\text{-}C_{10})$alkyl group, and
- Y represents a reactive function which can be activated by click chemistry, selected from the group comprising the azides, alkynes, cycloalkynes and conjugated dienes, in particular a compound according to claim 1 and in that it comprises the following steps:
  - bringing said compound into contact with a biomolecule,
  - bringing said compound bound to the biomolecule into contact with the target molecule and if necessary,
  - isolating the coupling product.

6. Method according to claim 5 characterized in that the biomolecule(s) involved in said coupling method are selected from the group comprising proteins, peptides, DNA, biological markers, hormones, vitamins, antibodies, polyamines, monosaccharides, oligosaccharides and polysaccharides, and molecules of biological interest of medicinal or label type.

7. Diagnostic reagent characterized in that it utilizes at least one compound according to claim 1.

8. Method of using a compound of formula (I) in which
- $R_1$ and $R_2$ represent independently of one another a $(C_1\text{-}C_{10})$alkyl group, a $(C_2\text{-}C_6)$cycloalkyl group, an aryl group, an aryl$(C_1\text{-}C_{10})$alkyl group, or a heterocyclic group,
- $R_3$ and $R_4$ represent independently of one another a hydrogen atom, a $(C_1\text{-}C_{10})$alkyl group, an aryl group or an aryl$(C_1\text{-}C_{10})$alkyl group, and
- Y represents a reactive function which can be activated by click chemistry, selected from the group comprising the azides, alkynes, cycloalkynes and conjugated dienes, as a diagnostic reagent.

9. Kit for the implementation of a coupling and bioconjugation method for coupling a biomolecule and a target molecule selected from the group comprising a molecule of biological interest, a natural or synthetic polymer, and a reactive surface which comprises at least one compound according to claim 1.

10. Method for the separation, detection and/or characterization of at least one molecule of interest potentially present in a medium, characterized in that it comprises at least one step of utilizing a kit according to claim 9 or at least one step of utilizing a compound of formula (I)

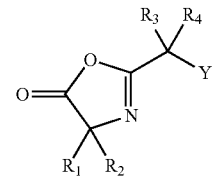

in which
- $R_1$ and $R_2$ represent independently of one another a $(C_1\text{-}C_{10})$alkyl group, a $(C_2\text{-}C_6)$cycloalkyl group, an aryl group, an aryl$(C_1\text{-}C_{10})$alkyl group, or a heterocyclic group,
- $R_3$ and $R_4$ represent independently of one another a hydrogen atom, a $(C_1\text{-}C_{10})$alkyl group, an aryl group or an aryl$(C_1\text{-}C_{10})$alkyl group, and
- Y represents a reactive function which can be activated by click chemistry, selected from the group comprising the azides, alkynes, cycloalkynes and conjugated dienes.

11. Composition comprising a compound according to claim 1 in combination with an aqueous or organic medium.

* * * * *